United States Patent [19]

Gavras

[11] Patent Number: 5,567,706
[45] Date of Patent: Oct. 22, 1996

[54] METHOD FOR TREATING IMPOTENCE

[76] Inventor: Haralambos Gavras, 8 Stevens Rd., Marblehead, Mass. 01945

[21] Appl. No.: 284,744

[22] Filed: Aug. 2, 1994

Related U.S. Application Data

[63] Continuation of Ser. No. 15,592, Feb. 10, 1993, abandoned.

[51] Int. Cl.⁶ .......................... A61K 31/44; A61K 31/49; A61K 31/50
[52] U.S. Cl. ............................. 514/280; 514/254
[58] Field of Search ...................... 514/280, 254

[56] References Cited

U.S. PATENT DOCUMENTS

| | | | |
|---|---|---|---|
| 4,310,524 | 1/1982 | Ursillo et al. | 424/244 |
| 4,532,135 | 7/1985 | Edwards | 519/222 |
| 4,659,714 | 4/1987 | Wart-Smith | 514/260 |
| 5,145,852 | 9/1992 | Virag | 514/253 |

OTHER PUBLICATIONS

Yajima et al., *Chemical Abstracts*, vol. 112, No. 13, p. 69, abstract No. 112020u, 1990.
Chemical Abstracts 112: 211365A (1990).

*Primary Examiner*—Marianne M. Cintins
*Assistant Examiner*—William R. A. Jarvis

[57] ABSTRACT

A method of treating impotency in men using a pharmaceutical composition having an effective amount for treating impotency of a selective post-synaptic peripheral $\alpha_1$-adrenoceptor antagonist having antihypertensive characteristics, and yohimbine, a central and peripheral $\alpha_2$-adrenoceptor inhibitor and parasympathetic agonist.

5 Claims, No Drawings

METHOD FOR TREATING IMPOTENCE

This application is a continuation, of application No. 08/015,592 filed Feb. 10, 1993, now abandoned.

BACKGROUND OF THE INVENTION

The present invention relates to a pharmaceutical composition for treatment of impotency in men and method of administering same.

Functional impotence is commonly associated with hypertension and is one of the most common side effects of many antihypertensive medications. It is a major cause of non-compliance with antihypertensive treatment. Medication to enhance sexual potency in men is known, but physicians are often reluctant to prescribe such medication because its main side effect is to raise blood pressure.

There is, therefore, a need for a medication that can effectively treat impotence without raising blood pressure, and similarly, a medication that can effectively treat hypertension without the resultant common side effect of impotence.

OBJECTS OF THE INVENTION

Accordingly, it is an object of the present invention to provide a method of treating impotence without causing hypertension.

Another object of the invention is to provide a method of treating impotence and hypertension.

Another object of the invention is to provide a method of treating hypertension without causing impotence.

A further object of the invention is to provide a method of treating impotence with α-adrenoceptor inhibitors having antihypertensive effect.

These and other objects of the invention will become apparent in the light of the accompanying disclosure.

SUMMARY OF THE INVENTION

The method and composition of the present invention achieve these and other objects by administration of and treatment for impotency in men with a pharmaceutical composition having an effective amount for treating impotency of a selective post-synaptic peripheral $\alpha_1$-adrenoceptor antagonist having antihypertensive characteristics, and yohimbine, a central and peripheral $\alpha_2$-adrenoceptor inhibitor and parasympathetic agonist.

DETAILED DESCRIPTION OF THE INVENTION

The sexual function is governed by the central and peripheral autonomic nervous system and is impaired in patients with autonomic dysfunction. Central α2-adrenoceptors are crucial in the regulation of this function by changing the level of sympathetic outflow. Stimulation of the presynaptic central $\alpha_2$-adrenoceptors exerts a sympathoinhibitory effect, leading to impotence. A typical example of this is the antihypertensive drug clonidine, a central $\alpha_2$-agonist with excellent antihypertensive effect associated very frequently with impotence. Inhibition of these same receptors with the $\alpha_2$-antagonist yohimbine is known to enhance sexual function by disinhibiting the central sympathoinhibitory neurons and increasing the sympathetic outflow to the periphery, which almost invariably raises also the blood pressure. Hence, use of yohimbine is restricted for fear of hypertensive cardiovascular complications. Prazosin is a peripheral $\alpha_1$-adrenoceptor antagonist which causes vasodilation and lowers blood pressure by inhibiting the action of catecholamines on the vascular $\alpha_1$-adrenergic receptors. It is a common antihypertensive agent and has also been used locally by intracorporeal injection for treatment of functional impotence, with proven success, but limited applicability, because of the need and timing of parenteral administration. Other post-synaptic peripheral $\alpha_1$-adrenoceptor antagonists such as doxazosin, terazosin, etc. may be used.

Vasoconstriction in response to elevated catecholamines is mediated mostly via stimulation of peripheral $\alpha_1$-adrenoceptors, and partly, about 20%, via stimulation of peripheral post-synaptic $\alpha_2$-adrenoceptors in the vascular wall. Blockade of either type of peripheral α-adrenoceptors by a specific inhibitor causes fall of blood pressure. Thus, the $\alpha_2$-antagonist yohimbine acting peripherally would also produce some blood pressure lowering, but this effect is far outweighed by its action on the central presynaptic $\alpha_1$-adrenoceptors that increase the sympathetic outflow to the periphery and cause intense vasoconstriction mediated via the overriding stimulation of peripheral $\alpha_1$-adrenoceptors. Hence, when the two drugs are used in combination, the low dose prazosin would prevent the yohimbine-induced blood pressure rise, whereas the high dose prazosin would produce an antihypertensive effect, and both would allow the additional small peripheral blood pressure lowering effect of yohimbine itself to become manifest.

Yohimbine has a central $\alpha_2$-blocking effect, that results in disinhibition of central sympathoinhibitory neurons and causes a hyperadrenergic state that raises blood pressure via stimulation of peripheral vasopressor $\alpha_1$-adrenoceptors. With the combined use of prazosin, however, these $\alpha_1$-receptors are already blocked. Yohimbine also has a blocking effect on peripheral vascular $\alpha_2$-adrenoceptors, that are also vasopressor, although less so than the vascular $\alpha_1$-receptors. This accounts for the drop of blood pressure below that expected for prazosin alone. Yohimbine is also known to have a parasympathetic agonistic effect, that accounts for the lack of increase, or slight decrease, in heart rate and for the beneficial effect on sexual impotence via its action on the arterioles and venules of the penile corpora cavernosa. From these interactions, it is apparent that the combination of yohimbine and prazosin has the unique properties of specifically enhancing cavernosal erectile function despite increased central sympathetic outflow, maintaining a status of balanced sympathetic-parasympathetic influence on the heart, inhibiting peripheral vasopressor $\alpha_1$- and $\alpha_2$-adrenergic vascular receptors. Varying the dose of prazosin administered such that it is lower in normotensive men and higher in hypertensive men, maintains the blood pressure or induces a decrease in systemic blood pressure.

The following example is provided solely as a non-restrictive illustration of the effect described above and to provide a clearer understanding of the advantage of the invention.

Clinical studies were conducted on hypertensive men having impotence associated with antihypertensive treatment. Prazosin, 5 mg, taken orally three times daily, reduced blood pressure without resolving the impotence. Addition of yohimbine, 5 mg, to the prazosin, 5 mg, taken orally three times daily, reduced blood pressure an additional 2–5 mmHg below that resulting from prazosin alone, without a change in heart rate, and additionally resolved the impotence.

What is claimed is:

1. A method of treating impotency in a male patient comprising administering orally to said male patient an effective amount for treating impotency of a selective postsynaptic peripheral $\alpha_1$-adrenoceptor antagonist having antihypertensive characteristics, and yohimbine, having central and peripheral $\alpha_2$-adrenoceptor inhibitor activity and a parasympathetic agonist effect.

2. A method of treating impotency in a male patient in accordance with claim 1 wherein the $\alpha_1$-adrenoceptor antagonist administered is prazosin.

3. A method of treating impotency in a male patient in accordance with claim 1 wherein the $\alpha_1$-adrenoceptor antagonist prazosin is administered in an amount from about 1 mg to about 10 mg.

4. A method of treating impotency in a male patient in accordance with claim 1 wherein the $\alpha_2$-adrenoceptor inhibitor yohimbine is administered in an amount of about 5 mg.

5. A method of treating impotency in a male patient comprising administering orally to said male patient an effective amount for treating impotency of a selective postsynaptic peripheral $\alpha_1$-adrenoceptor antagonist having antihypertensive characteristics, and a central and peripheral $\alpha_2$-adrenoceptor inhibitor having parasympathetic agonist and central sympathetic enhancing effect.

* * * * *